(12) United States Patent
Yu et al.

(10) Patent No.: US 7,799,191 B2
(45) Date of Patent: *Sep. 21, 2010

(54) EPOXY ENHANCED POLYMER MEMBRANE TO INCREASE DURABILITY OF BIOSENSORS

(75) Inventors: Bazhang Yu, Tampa, FL (US); Francis Moussy, Tampa, FL (US)

(73) Assignee: University of South Florida, Tampa, FL (US)

( * ) Notice: Subject to any disclaimer, the term of this patent is extended or adjusted under 35 U.S.C. 154(b) by 13 days.

This patent is subject to a terminal disclaimer.

(21) Appl. No.: 12/015,614

(22) Filed: Jan. 17, 2008

(65) Prior Publication Data

US 2008/0206829 A1     Aug. 28, 2008

Related U.S. Application Data

(63) Continuation of application No. 11/161,979, filed on Aug. 24, 2005, now Pat. No. 7,534,330.

(60) Provisional application No. 60/522,168, filed on Aug. 24, 2004.

(51) Int. Cl.
    C25B 9/02    (2006.01)
    B32B 27/38   (2006.01)
    C08L 63/00   (2006.01)
    C12Q 1/00    (2006.01)
    G01N 33/50   (2006.01)

(52) U.S. Cl. ............... 204/403.11; 204/403.01; 204/403.06; 204/403.1; 204/403.14; 428/413; 428/418; 523/113; 525/523

(58) Field of Classification Search ............ None
    See application file for complete search history.

(56) References Cited

U.S. PATENT DOCUMENTS

| | | | |
|---|---|---|---|
| 3,945,964 A * | 3/1976 | Hastings et al. | 523/406 |
| 4,418,148 A | 11/1983 | Oberhardt | |
| 5,165,407 A * | 11/1992 | Wilson et al. | 600/345 |
| 5,223,124 A | 6/1993 | Ege | |
| 5,322,063 A | 6/1994 | Allen et al. | |
| 5,428,083 A * | 6/1995 | Smith et al. | 523/414 |
| 5,773,270 A | 6/1998 | D'Orazio et al. | |
| 6,162,611 A * | 12/2000 | Heller et al. | 435/14 |
| 6,343,225 B1 | 1/2002 | Clark, Jr. | |
| 6,514,718 B2 | 2/2003 | Heller et al. | |
| 6,654,625 B1 * | 11/2003 | Say et al. | 600/347 |
| 7,534,330 B2 * | 5/2009 | Yu et al. | 204/403.11 |
| 2003/0042137 A1 * | 3/2003 | Mao et al. | 204/403.01 |
| 2003/0070548 A1 | 4/2003 | Clausen | |

* cited by examiner

Primary Examiner—Michael J Feely
(74) Attorney, Agent, or Firm—Michele L. Lawson; Smith & Hopen, P.A.

(57) ABSTRACT

The present invention provides a polymer membrane enhanced with cured epoxy resin for use as the outer membrane of biosensors. The membrane includes approximately 30-80% epoxy resin adhesives, 10-60% polymer such as poly (vinyl chloride), polycarbonate and polyurethane and 0-30% plasticizers and 5-15% surface modifier reagent such as polyethylene oxide-containing block copolymers. Utilizing the polymer membrane of the present invention, a three-layered sensing element has been developed. This sensing element will be particularly useful for miniaturized biosensors used for in vitro blood measurements or for continuous in vivo monitoring such as implantable biosensors. This element includes an enzyme layer, an interference-eliminating layer and the novel polymer member of the present invention as the outer polymer layer. This novel sensing element shows excellent response characteristics in solutions and has an extremely long lifetime. This technology is particularly useful for improving the lifetime of implantable biosensors.

15 Claims, 8 Drawing Sheets

US 7,799,191 B2

EPOXY ENHANCED POLYMER MEMBRANE TO INCREASE DURABILITY OF BIOSENSORS

CROSS-REFERENCES TO RELATED APPLICATIONS

This application is continuation of U.S. patent application Ser. No. 11/161,979 filed Aug. 24, 2005 (now U.S. Pat. No. 7,534,330), the contents of which are herein incorporated by reference, which claims the benefit of U.S. Provisional Application No. 60/522,168, filed Aug. 24, 2004.

STATEMENT REGARDING FEDERALLY SPONSORED RESEARCH OR DEVELOPMENT

This work has been supported by grants from the NIH/NIBIB (Grant No. 1 R01 EB01640.01).

FIELD OF INVENTION

This invention pertains to enzyme biosensors. More particularly, this invention pertains to a polymer membrane enhanced with cured epoxy resin for use as the protective membrane of enzyme biosensors such as implantable glucose biosensors.

BACKGROUND OF INVENTION

The lifetime of enzyme biosensors is highly dependent upon the stability and the amount of immobilized enzyme inside the sensing element that is generally composed of an enzyme-containing multilayer membrane. How to most effectively prevent the loss of enzyme from the sensing element when a biosensor is used repeatedly or continuously remains a difficult problem. Most commercially available biosensors used in the food industry, environmental monitoring and blood analysis are based on replaceable sensing elements. Therefore, the lifetime of such a biosensor may be extended limitlessly by replacing the sensing element. Unfortunately, the replacement of the sensing element is not feasible for miniaturized biosensors, especially for implantable biosensors.

Miniaturized biosensors are well suited for continuous and in situ field monitoring. They have an obvious significance for medical applications. This is because a small biosensor needs only a small amount of sample for analysis and results in minimal surgical trauma when implanted for in vivo analysis. The most important progress made by miniaturized biosensors is to lead to the application of inexpensive, disposable maintenance-free biosensors in clinical and biomedical areas. Typical examples are i-STAT silicon-based single-use biosensors, FreeStyle™, TheraSense electrochemical test strips for blood glucose. Single-use biosensors are produced in mass by thin film fabrication technology and have a very good sensor-sensor consistency. The same technology is also used to manufacture miniaturized biosensors with a relatively long lifetime for critical care analysis, e.g. GEM Premier™. The lifetime of such a miniaturized biosensor is typically in the range of 2-8 weeks in continuous use with minimal maintenance. The lifetime is even less if it is used for implantation. A flexible sensor designed for subcutaneous in vivo amperometric monitoring of glucose was disclosed in U.S. Pat. No. 6,514,718 to Heller et al. The typical three or four-layered sensing element was employed in this sensor. The layers included an enzyme layer, a glucose flux limiting layer, a horseradish-peroxidase-based interference-eliminating layer and a biocompatible layer. The sensing element is formed within a recess upon the tip of a polymide insulated gold wire. The location of the sensing element requires stringent preparation techniques and allows for only a limited space for enzyme loading. To improve the response characteristics of an implantable glucose sensor in a low oxygen environment, a new kind of sensing element containing perfluorocarbon emulsion has recently been introduced (Analy Chim Acta 411 (2000) 187-192; see also U.S. Pat. No. 6,343,225 to Clark, Jr.). However, the application of this technology in the field of miniaturized biosensors may be limited because the presence of perfluorocarbon, which inevitably causes phase separation in sensing membranes, thereby impairing response stability as well as shortening the lifetime of the sensor.

The long-term stability of the sensing element is the development bottleneck of implantable biosensors. Various efforts have been made on improving the lifetime of implantable glucose biosensors over the past 30 years, but essential breakthroughs have materialized. The remaining difficulties with long-term implantable biosensors mainly originate from the strict requirements of implantation applications. To minimize surgical injury and discomfort caused by implantation, the probe size (diameter) is generally required not to exceed 1 millimeter. Thus, many of the mature fabrication technologies used for conventional biosensors are not applicable for implantable biosensors. In addition, the measurement environment for implanted biosensors is much more aggressive than blood or solutions. Therefore, an implantable glucose biosensor can only last for a few days in the body. So far, such biosensors are mainly used to provide a continuous real-time glucose variation profile for diagnostic and treatment optimization. Only a couple of continuous glucose monitoring devices have been successfully used for short-term glucose measurements in the skin by diabetes patients (e.g. Mini GGMS® and GlucoWatch®).

The function failure of an enzyme biosensor is mainly a result of the following three factors:

The loss of enzyme activity and/or the enzyme itself, including the separation of enzyme layer from the electrode surface;

Degradation of the polymer membrane (This can result from decomposition and physical damage of outer membrane, leakage of the sealing interface between membrane and electrode); and Biological contamination of the outer membrane.

Using an adequate enzyme methodology is extremely important for the construction of a long-term, stable, miniaturized biosensor. Free enzyme loses more than 80% of its activity after one week in a solution, while immobilized enzyme can maintain catalytic activity for months and even years. Methods used to immobilize enzymes in biosensors include (1) adsorption; (2) physical entrapment; (3) chemical cross-linking; (4) covalent coupling; and (5) co-deposition. Among the various methods, the cross-linking method is most frequently used because it has the advantage of the covalent bonding, high enzyme loading and small loss of enzyme activity. Cross-linking agents, e.g. glutaraldehyde, bisisocyanate, bisdiazobenidine and chromium acetate are often used together with functionally inert proteins such as bovine serum albumin (BSA) and gelatin. The enzyme can also be cross-linked with epoxy resins as described in Biosensor and Bioelectronics, 11(8), 735-742 (1996). The disadvantage of chemical cross-linking is that the resulting cross-linking tends to separate from the electrode surface after wetting due to the poor adhesion of the gel layer to the electrode. Conversely, an electrodeposited enzyme layer has a stronger bond with the electrode surface, but the enzyme loading is very small. Electrochemical formation of non-conductive polymer is self-limiting, so the thickness generally does not exceed 100 nm.

The polymer membrane plays the role of enzyme layer protection and provides a diffusion-limiting barrier. It is readily understood that the property of the polymer can influence the biosensor's long-term performance. In many cases, the polymer membrane consists of several different polymer layers to obtain certain specific properties such as optimal response stability, good mechanical strength, high diffusion resistance for unexpected species and macromolecules and biocompatibility [see for instance U.S. Pat. Nos. 6,514,718, 5,773,270 and 4,418,148]. Unfortunately, true multi-layered polymer membranes cannot be realistically achieved by coating due to problems of inter-solubility and phase separation of polymers. Furthermore, multilayered membranes result in excess thickness which rapidly increases the response time of the sensor.

For these reasons, employing a layer of polymer membrane is an attractive option for overcoming the aforementioned limitations. Various polymer and copolymer materials have been investigated for biosensors, e.g. Nafion®, polydimethylsiloxane (PDMS), polycarbonate (PC), polyurethane (PU), poly(vinyl chloride) (PVC), cellulose acetate (CA), tetrafluoroethylene (Bull. Krean Chem. Soc., 24(4), 2003, 514-516), perfluorocarbon polymer (T. Matsumoto et al. Biosensors & Bioelectronics 16 (2001) 271-276), UV-curable epoxy acrylates (E.P. Pat. No. 1,292,823 (2003)) vinyl polymer with a siloxane region and epoxy group (J.P. Pat. No. 03,024,757) and polyallylamine-polyaziridine (U.S. Pat. No. 6,514,718). The selection of suitable polymers for sensing elements has a profound influence on the long-term properties of the resulting biosensor. The polymer layer should result in minimal adhesion of proteins and cells. Studies have addressed improving the physical nature of polymer membranes using various additives such as plasticizers according to the modification method of commercial films. For instance, using a plasticizer may interpose itself between the polymer chains and interact with the forces held together by extending and softening the polymer matrix and possibly leading to some improvement in brittleness, flexibility and strength, as well as increasing the adhesiveness of the film with other surfaces or layers.

For implantation applications, the additives must not cause toxicity as they leach out of the membrane. Furthermore, the polymer must have excellent biocompatibility. The fouling of biosensors commonly results from tissue reactions in the microenvironment around the membrane and microorganism deposition on it. Tissue reactions cause an increase in the diffusion resistance of the analyte and oxygen or can result in aberrant analyte distribution, and even cause failure of response. Improving the surface adsorption characteristic of the outermost membrane may inhibit the fouling tendency of a biosensor.

SUMMARY OF INVENTION

This invention provides an epoxy-enhanced polymer membrane ("epoxy polymer membrane") that is adequate to be use as the protective membrane of biosensors, particularly adequate for implantable biosensors which are intended to work under the skin or in the body for long time. The epoxy polymer membrane can form a coating or layer in a multi-layered biosensor. By multilayered it is meant that there are two or more layers surrounding an electrode. It is found that an epoxy polymer membrane imparts the desirable property of increasing the in vivo durability of the biosensor during long-term implantation. This invention also provides a method for the preparation of coil-type implantable glucose sensor thereof, a multilayered sensing element including at least one the said epoxy-enhanced polymer membrane and at least one immobilized enzyme layer.

The multilayered sensing elements will include an immobilized enzyme layer formed on the surface of an electrode and an epoxy polymer layer. The epoxy polymer layer will be an external layer relative to the immobilized enzyme layer. Thus, the epoxy polymer layer will add durability to the underlying enzyme layer, while also, in certain configurations, serving as a diffusion barrier to the internal enzyme layer. Certain embodiments will further include an interference-eliminating layer. The interference-eliminating layer can be spaced between the immobilized enzyme layer and the epoxy polymer layer. It is found that perfluorinated polymers containing small proportions of sulfonic or carboxylic ionic functional groups, such as Nafion, are advantageous as the interference eliminating layer. The said sensing element can be used to significantly improve the long-term stability of miniaturized biosensors whose sensing membrane is required to directly form upon the electrode by thin film fabrication technology such as casting, coating, screen-printing or deposition. The said miniaturized biosensors can be used in the field of biomedical measurement and continuous monitoring, especially for implantation applications.

An advantageous epoxy-enhanced polymer membrane is made of a mixture comprising about 30-80% (by weight) of a polymer and about 10%-60% epoxy resin adhesive. Often the polymer will be a castable polymer which will adopt a shape as the polymer forms. Such an advantageous epoxy-enhanced polymer membrane can further comprise about 5-15% polyethylene oxide-containing block copolymer. In addition, 0-30% plasticizers can be added in the mixture as needed. A particularly advantageous epoxy polymer membrane comprises about 40% to about 70% by weight of polymer, about 30% to about 50% by weight of epoxy resin adhesive, about 5% to about 10% by weight of polyethylene oxide-containing block copolymer and up to about 30% by weight of a plasticizer.

The said polymer can be polydimethylsiloxane, polycarbonate, poly(vinyl chloride), cellulose acetate, polyallylamine-polyaziridine, polyvinylidene chlorides, polyvinylidene-acrylonitrile copolymer, polyacrylates, polymethacrylates, polystyrenes, polyesters, polyurethanes or the like. It is generally preferable that the polymer be biocompatible, which, for example, can be synthesized from polymers including biocompatible polyesters, polyurethane and copolymers containing phosphorylcholine.

The said epoxy resins can be cured either by light and radiation or by heat with curing agents, e.g. cycloaliphatic, amine-cured and anhydride cured epoxy resins, preferably, amine-cured epoxy resins with a curing temperature less than 120° C. It is important that the curing temperature not be too high to prevent destruction of the enzyme. Likewise, care should be exercised to prevent excess radiation or UV light to preserve enzyme activity. thus preventing Typical amine-cured epoxy resins are various diepoxy and polyepoxy such as diglycidyl ether of bisphenol A (DGEBA), aliphatic diepoxide, poly(propylene glycol) diglycidyl ether while typical curing agents are dicyandiamide, diaminodiphenylmethane (DDM), diethylenetriamine (DTA), cyclohexylmethylamine (CMA), polyoxypropyleneamine, 5-amino-1,3,3-trimethyl-cyclohexanemethylamine. Epoxy-modified polymers such as glycidyl-terminated polyurethane (Polymer International, 35, 361-370 (1994)) may be also used for the present invention. Various commercially available epoxy resin adhesives including additives, accelerators, promoters, plasticizers and filling materials are available if specific membrane properties are needed. It is to be noted that some additives may be biologically hazardous once they leak out into the surrounding tissue or electroactive at the applied potential so the selection may be done in a prudent way. For in vivo application, simpler and purer epoxy resins are often advantageous.

The said polyethylene oxide-containing block copolymer is usually used as blood-compatible surface modifiers. Such copolymers have low interfacial free energy with water, high surface mobility, unique solution properties and molecular conformation, good hydrophilicity, and steric stabilization effects (Prog Polym Sci, 20, 1043-1079 (1995)). Typical polyethylene oxide-containing block copolymers may be non-ionic polyethylene and polypropylene glycol (Synperonic surfactants) or polyethylene glycol ether (Brij surfactants). As the polymer is high biocompatible, e.g. polyurethane, polyethylene oxide-containing block copolymer may be not necessary.

The said epoxy-enhanced polymer membrane may have selectively added plasticisers which are used to improve the extensibility of polymer blend as well as reduce phase separation. In a high epoxy/polymer ratio (e.g. >1:1 (wt.), the membrane becomes fragile so plasticizers are needed. Typical plasticizers may be phthalate, sebacate and phosphate such as dibutyl phthalate, butyl sebacate and triphenyl phosphate. In a low epoxy/polymer ratio, or when highly epoxy resin compatible polymer is used, plasticizers may be not necessary.

Epoxy resin produces a big molecular network and can act as a backbone of polymer film. The epoxy network has very good structural stability and mechanical strength and hence significantly extends the membrane lifetime in aqueous solutions. The presence of polymer probably decreases the curing rate of epoxy resins, but does not affect the overall curing mechanism (Macromolecules, 29, 499-506 (1996)). In fact, the presence of polymer neutralizes the fragility and diffusion resistance of epoxy membranes while epoxy resin reinforces the durability and adhesion of the polymer membrane.

The excellent adhesion of epoxy resin eliminates the peel-off risk of the outer polymer membrane from both the beneath enzyme layer and electrode surface. Therefore, the leakage of enzyme is effectively inhibited. It can be predicted that the adhesion of epoxy-enhanced polymer to nonmetal substrates in wafer type or thin film type biosensors is more reliable and more probably bears the stress caused by swelling of enzyme layer.

When a biocompatible polymer is selected such as polyurethane, the said epoxy-enhanced polymer membrane can be directly used as the outermost membrane of implantable biosensors instead of a polyurethane coating because hydrophobic epoxy resins can also have very good biocompatibility (Cell Physiol Biochem.; 13(3), 155-164 (2003)). This extremely simplifies the sensing element construct and avoids the inter-solubility of multiple layer polymers.

When the less biocompatible polymer is selected such as poly(vinyl chloride), an additional biocompatible polymer used as outer-layer, typically polyurethane, hydrogel or a copolymer containing phosphorylcholine, is probably needed for in-vitro and in vivo biosensors. The bi-layered polymer membrane can tightly couple after epoxy resins curing.

The said immobilized enzyme layer is formed by chemical cross-linking method. Chemical cross-linking can be achieved by mixing a cross-linking agent, typically e.g. glutaraldehyde (GA), glycidyl methacrylate (GMA), polyhydroxyethyl methacrylate, butyl methacrylate (BMA), hexamethylenediamine (H M DA), bissisocyanate, bisdiazobenidine, epoxy resins or chromium acetate. Functionally inert protein such as bovine serum albumin (BSA) or gelatin can be selectively used for enzyme immobilization.

The said immobilized layer can also contain electron transfer mediators, preferably ferrocene and osmium complex.

In addition to the immobilized enzyme layer and the epoxy-enhanced polymer membrane, the sensing element can further contain an interference-eliminating layer which is formed either directly at the electrode surface or in between the enzyme immobilized layer and the epoxy-enhanced polymer membrane.

The internal interference-eliminating layer preferably is enzyme-entrapped electropolymerized layer. The entrapped enzyme, typically glucose oxidase (GOx), chemically binds with cross-linking agents and forms active sites at the electrode surface. Electropolymerization can be achieved by using nonconducting polymers such as poly(o-phenylenediamine), poly(mphenylenediamine) (PMPD), poly(p-phenylenediamine), polyphenol, overoxidized polypyrrole, overoxidized polyaniline and the like. The internal electropolymerized film can drastically reduces the effects of electrochemically active interferents, such as L-ascorbic acid and uric acid (Anal chem. 62, 1111-1117 (1990)).

The internal electropolymerized film can not only reject electroactive interferents but also electrode fouling species (e.g. protein). In other words, the internal film can partially inhibit the sensitivity deceasing of the sensor in subcutaneous tissue or in blood specimens (Clin Chem, 45(2), p 283-285 (1999)). The middle interference-eliminating layer may be a Nafion layer.

The said enzyme layer is formed either by electropolymerization (electrochemical deposition) or by chemical cross-linking. An enzyme, typically glucose oxidase (GOx), is entrapped during the electropolymerization or chemically binds with cross-linking agents. Electrochemical deposition provides reproducible and site-selective immobilization of enzyme but has a low enzyme loading. Conversely, chemical cross-linking provides a relatively high enzyme loading but has poor joint strength with a metal electrode. A preferable solution is that the enzyme layer is first electrodepositioned to the electrode then further thickened by chemical cross-linking method. Electropolymerization can be achieved by using nonconducting polymers such as poly(o-phenylenediamine), poly(m-phenylenediamine) (PMPD), poly(p-phenylenediamine), polyphenol, overoxidized polypyrrole, overoxidized polyaniline and the like. Chemical cross-linking can be achieved by mixing a cross-linking agent, typically e.g. glutaraldehyde (GA), glycidyl methacrylate (GMA), butyl methacrylate (BMA), hexamethylenediamine (HMDA), bissisocyanate, bisdiazobenidine or chromium acetate with functionally inert protein such as bovine serum albumin (BSA) or gelatin.

The multi-layered sensing element can include an intermediate interference-eliminating layer between the immobilized enzyme layer and the epoxy polymer layer. An advantageous intermediate layer is a persulfonate ionomer, such as Nafion®. Nafion® is a product of DuPont. Nafion® is a perfluorinated polymer that contains small proportions of sulfonic or carboxylic ionic functional groups. Its general chemical structure can be seen below, where X is either a sulfonic or carboxylic functional group and M is either a metal cation in the neutralized form or an $H^+$ in the acid form.

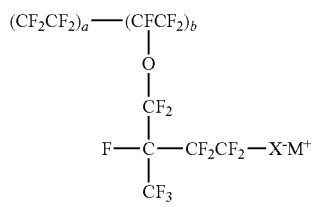

Nafion® Perfluorinated Ionomer

Because of its excellent ionic transport properties, selectivity, mechanical strength, and insolubility in water, Nafion® has been extensively used as the outer membrane of sensors. The Nafion® polymer structure may be illustrated by using Yeager Model based on a three-phase clustered system with interconnecting channels within the polymer (Yeager, H. J.; Eisenberg, A, *American Chemical Society*: Washington, D.C., 1982, pp. 1-6, 41-63). The three regions consist of (A) a fluorocarbon backbone, (B) an interfacial region of relatively large fractional void volume containing some pendant side chains, some water, and those sulfate or carboxylic groups and counter ions which are not in clusters, and (C) the clustered regions where the majority of the ionic exchange sites, counter ions, and sobbed water exists. Yeager Model may be simplified into discrete hydrophobic and hydrophilic regions. The hydrophobic region is composed of the polymer fluorocarbon backbone. Conversely, the hydrophilic region contains the ionic groups and their counter. The hydrophobic regions including fluoride vinyl ether and bridge oxygen can incorporate with other polymers through intermolecular interaction such as Van der Waals or hydrogen bonds. On the other hand, the presence of electrostatic interactions between the ions and the ion pairs enhances the intermolecular forces between the hydrophilic regions and the enzyme layer. Thus Nafion® serves not only as an interference-preventing layer against the diffusion of negatively charged ions such as ascorbic acid and uric acid but also as a bridge layer between the highly hydrophilic enzyme layer and the highly hydrophobic polymer membrane.

Nafion®, made from Nafion® perfluorinated ion-exchange resin in hydrogen form, has very good electrochemical performance and been extensively used as the outer membrane of biosensors. High temperature cured Nafion membrane shows excellent long-term stability and hence is one of the best selections for miniaturized biosensors. The fatal shortness of Nafion membrane is that it might be mineralized by the deposited calcium phosphates during implantation.

To avoid Nafion® mineralization, the Nafion® layer is covered with a polymer protection layer. The said polymer layer has better durability and mineralization resistance than Nafion as well as exhibiting a strong adherence to the Nafion layer. The said polymer layer contains at least polymer and epoxy resin adhesive, preferably polyethylene oxide-containing block copolymer. The said polymer is preferably polydimethylsiloxane, polycarbonate, polyurethane, poly poly (vinyl chloride), cellulose acetate, polyallylamine-polyaziridine or the like. The said epoxy resin adhesive can be cured either by light or radial or by heat with curing agents, e.g. cycloaliphatic, amine-cured and anhydride cured epoxy resins, preferably, amine-cured epoxy resins with a curing temperature less than 120° C. Typical amine-cured epoxy resins are various diepoxy and polyepoxy such as diglycidyl ether of bisphenol A (DGEBA), aliphatic diepoxide, poly (propylene glycol) diglycidyl ether while typical curing agents are dicyandiamide, diaminodiphenylmethane (DDM), diethylenetriamine (DTA), cyclohexylmethylamine (CMA), polyoxypropyleneamine, 5-amino-1,3,3-trimethylcyclohexanemethylamine. Epoxy-modified polymers such as glycidyl-terminated polyurethane (Chen-Chi M. Ma, Hung-Chung Hsia, Der-Shyang Chen, Ye-Shiu Li & Ming-Shiu Li, *POLYMER INTERNATIONAL VOL.* 35, NO. 4, 1994) may be also used for the present invention. Various commercially available epoxy resin adhesives including additives, accelerators, promoters, plasticizers and filling materials are available if specific membrane properties are needed. It is to be noted that some additives may be biologically hazardous if leaked out into the surrounding tissue or electroactive at the applied potential so the selection may be done in a prudent way. For in vivo application, simpler and purer epoxy resins are more preferable.

The said polymer layer may include selectively added plasticisers. Here plasticizers are used to improve the extensibility of polymer blend and reduce phase separation. In a high epoxy/polymer ratio, e.g. >50% (wt.), the membrane becomes fragile so plasticizers are needed. Typical plasticizers may be phthalate, sebacate and phosphate such as dibutyl phthalate, butyl sebacate and triphenyl phosphate. In low epoxy/polymer ratio, plasticizers are not necessary.

Cured epoxy resin produces a big molecular network and can act as a backbone of polymer film. The epoxy network has very good structural stability and mechanical strength and hence significantly extends the membrane lifetime in aqueous solutions. The presence of polymer probably decreases the curing rate of epoxy resins, but does not affect the overall curing mechanism (Ming-Shiu Li, Chen-Chi M. Ma, Jyh-Luen Chen, Miaw-Ling Lin and Feng-Chih Chang *Macromolecules, Vol.* 29, No. 2, 1996). In fact, the presence of castable polymer neutralizes the fragility and diffusion resistance of epoxy membranes while epoxy resin reinforces the durability and adhesion of the polymer membrane.

Due to the excellent adhesion property of epoxy resin to a wide scope of materials, the leakage of enzyme through the adhesion interface of the outer polymer and the metal electrode surface in needle-type biosensors is effectively inhibited. It can be predicted that the adhesion of epoxy-enhanced polymer to nonmetal substrates in wafer type or thin film type biosensors is more reliable and more probably bears the stress caused by enzyme layer swelling.

The mass transport of analyte is realized mainly through the polymer around the epoxy backbone. When the epoxy-polymer membrane is immersed in aqueous solutions, water molecules attack the epoxy network that is held together by hydrogen bonds and other secondary valence forces between adjacent polymer chains. Bond water induces swelling as well as allows for mass transport of analyte through the epoxy network itself.

More preferably, the surface hydrophobic property of the epoxy-polymer may be improved by adding polyethylene oxide-containing block copolymers, which are usually used as blood-compatible surface modifiers. Such copolymers have low interfacial free energy with water, high surface mobility, unique solution properties and molecular conformation, good hydrophilicity, and steric stabilization effects (Lee J H, Kopecek P. Andrade J D, *Blood Compatibility of polyethylene oxide surfaces. Prog Polym Sci* 1995; 20:1043-1079). Typical polyethylene oxide-containing block copolymers may be no-ionic polyethylene and polypropylene glycol (Synperonic surfactants) or polyethylene glycol ether (Brij surfactants).

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1A:
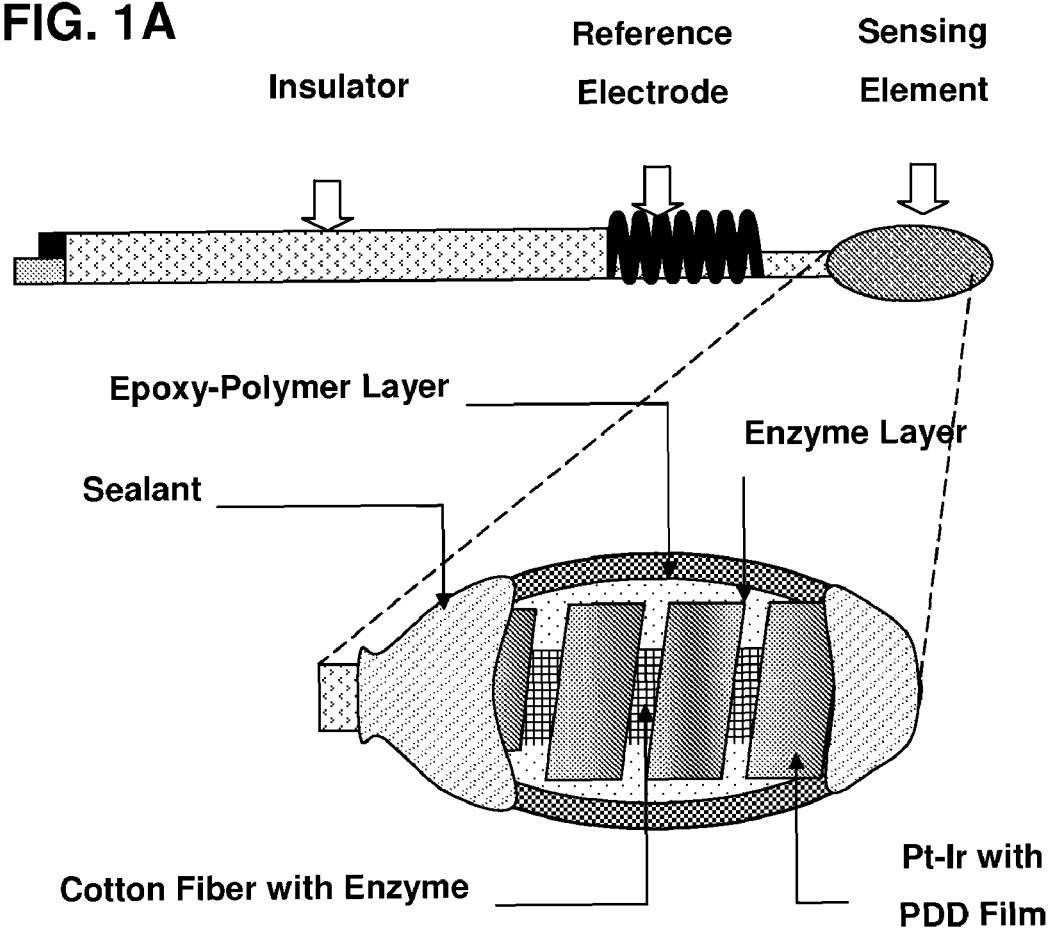
FIG. 1A is a schematic diagram of a coil-type biosensor, which may utilize the sensing element of the invention. PDD= (poly(ophenylenediamine) or poly(m-phenylenediamine); Not to scale.
Figure 1B:
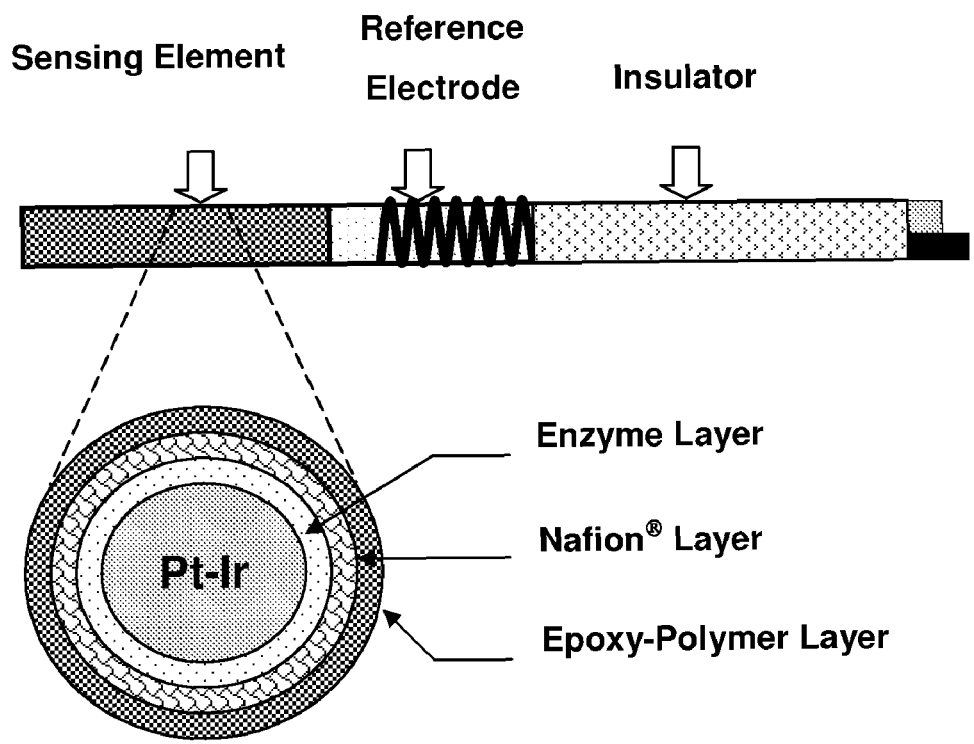
FIG. 1B is a schematic diagram of a needle-type biosensor, which may utilize the sensing element of the invention. PDD= (poly(ophenylenediamine) or poly(m-phenylenediamine); Not to scale.
Figure 1C:
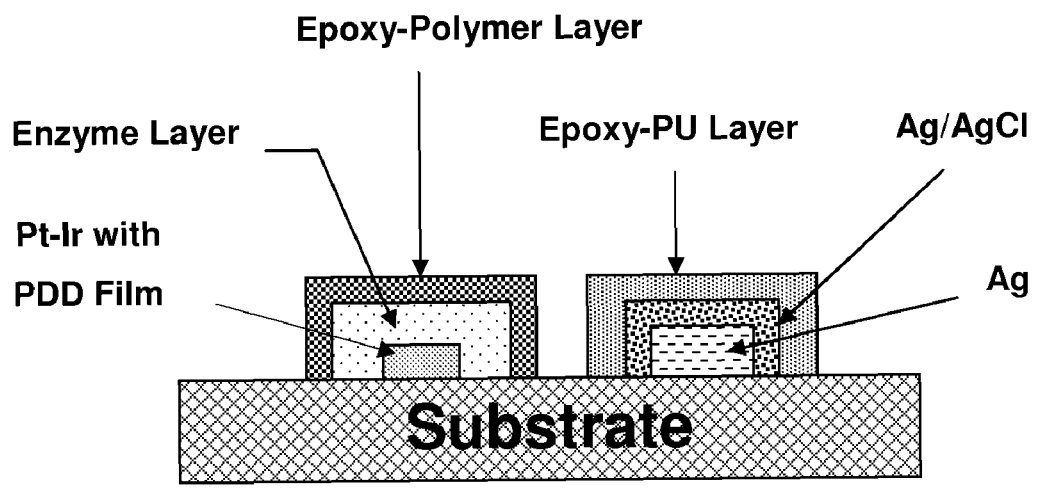
FIG. 1C is a schematic diagram of a cross-section of a chip biosensor, which may utilize the sensing element of the invention. PDD=(poly(ophenylenediamine) or poly(m-phenylenediamine); Not to scale.

Referring to FIG. 1, there are shown three kinds of possible biosensors, which may utilize the sensing element of the present invention. It is to be understood that the invention is not limited to these precise forms of biosensors, and that different biosensor constructs and methods may be used therein without departing from the scope of the invention.

An advantageous biosensor is designed according to electrochemistry principles and composed of a sensing element based on a conductor which may be platinum, gold, graphite or the like and a reference electrode based on silver, silver/silver chloride (Ag/AgCl) or the like. On the conductor, the sensing element containing at least one immobilized enzyme layer and one epoxy-enhanced polymer is formed by using coating, spreading, screen-printing and other adequate thin film techniques. Furthermore, the sensing element preferably has one internal interference-eliminating layer that is preferably formed by electrochemical polymerization or one middle interference-eliminating layer that is preferably is made of Nafion polymer. The sensing element is targeted to the construction of long-term miniaturized biosensors which are used for in vitro and in vivo medical measurements and on-line detection and monitoring of biological species in food industry and environmental chemistry, therefore, preferably has a sensing area of less than 20 $mm^2$, more preferably less than 4 $mm^2$.

FIG. 1 has shown three general types of biosensors which the invented sensing element is applicable for. Type A is designed in our laboratory and also used for implantation purposes. Type B is a typical needle-type implantable biosensor. Type C describes a radical construct of the thin film biosensor or the so-called chip biosensor where the invented sensing element can be formed in the substrate. The substrate may be rigid silicon, glass, ceramic, plastic, metal, alloy and the like as well as may be flexible plastic substrate. Type C biosensors with the invented sensing element may be expected to have a much longer lifetime than the similar biosensors used in in vitro measurements and is particularly suitable for implantation applications and in situ analysis which do not allow implementing any maintenance for the biosensor.

Although different fabrication technologies may be used and different polymer, epoxy resins, curing agents or additives may be involved for biosensors, the invented sensing element with an epoxy-enhanced polymer membrane can be anticipated to have some common features, i.e. the long-term performance of biosensors will be significantly enhanced due to the introduction of epoxy resins.

A coil-type glucose biosensor with the invented sensing membrane element was developed and the behavior of the biosensor was experimentally investigated. The coil-type has traits of small size and large sensing surface area and is particularly suitable for preparation and investigation in laboratories. The sensing membrane element is mainly constructed in the forms of PDD/GOx/epoxy-Polymer and GOx/Nafion/epoxy-Polymer. Epoxy network was introduced to polymer membrane structure by blending the commercial fast-cured epoxy-resin adhesive with polymer such as polycarbonates, poly(vinyl chloride) and polyurethane. The glucose oxidase was immobilized by chemical cross-linking method based on bovine serum albumin and glutaraldehyde.

Other sorts of commercial epoxy resins with and without hardeners may be used for the present purpose only if they do not contain electrochemical interference substances. Preferably, the epoxy resin can be fast cured at <120° C. with in 1 hour. The hardness or flexibility of the resulting membrane is mainly adjusted by varying the proportion of epoxy/polymer as well as by varying the proportion of hard/soft curing agents like epoxy embedding medium Epon 812-DDSA/MNA (Ultrastructure Research 365, 119-126 (1971). The preferable epoxy resins including curing agents in the membrane are 10-60% (w/w), and more preferably 30-50%. The preferable anhydride/epoxide molar ratio in the final mixture is 1:1. Polymer may be any materials which can be used for biosensors but must be compatible with the epoxy resins, preferably polycarbonate, polyurethane and PVC. The preferable percentage of polymer in the membrane is 30-80%, more preferably 40-70%. Furthermore, 0-30% plasticizer and 5-15% polyethylene glycol ether (Brij surfactants) may be selectively added to the polymer blend.

Exemplary Embodiment

Materials

Dextrose, Bovine serum albumin (BSA) and glutaraldehyde (50%) were obtained from Fisher Scientific. Bovine adult serum, glucose oxidase (GOD) (EC 1.1.3.4, Type X-S, *Aspergillus Niger*, 157,500 U/g, Sigma), ATACS 5104 epoxy adhesive, poly(vinyl chloride) (PVC), polycarbonate (PC), polyurethane (PU), isopropyl myristate (IMP), Aliquat 336 (AL), Brij 30, chloroform, tetrahydrofuran (THE), L-ascorbic acid, acetaminophen, uric acid and creatinine were obtained from Sigma-Aldrich. 0.125 mm Teflon-covered platinum-iridium (9:1 in weight) wire was obtained from World Precision Instruments, Inc. Electrically-insulating Sealant was purchased from North American Oil Company (Atlanta). ATACS 5104 (ATACS Products, Inc., Seattle) is a fast-cured two component adhesive composed of modified mercaptan curing agent (Part A) and epoxy resin composite (Part B) including 50-75% epoxy Novolac resin, 1-5% bisphenol-A epoxy resin and 20-50% Aliphatic Triglycidyl Ether.

Apparatus

Electrochemical experiments were performed with Model 263A potentiostat supported by PowerSuite Software (Princeton Applied Research) and Apollo 4000 Free Radical Analyzer (World Precision Instruments). The 10-ml electrochemical cell consisted of a glucose sensor and a saturated KCl calomel reference electrode (SCE, Sigma-Aldrich) or an Ag/AgCl wire electrode. Membrane morphometrics were observed and photographed under Leica S6D stereomicroscopy (Leica Microsystems Ltd.) and Philips 515 Scanning Electron Microscope. A FreeStyle™ blood glucose meter (Therasense, Alameda) was used to check the glucose concentration of serum specimens.

Sensor Fabrication

The coiled-wire-type biosensor (FIG. 1 (A)) can provide an excess enzyme loading for enzyme-catalyzed reaction of glucose for long time and thereby is particularly suitable for the present purpose on lifetime investigation of outer polymer membranes. For this reason, a series of coil-type sensors based on a coiled platinum-iridium have been fabricated according to the following procedures:

(1) Pt Wire Coiling

The platinum or silver electrode is formed by winding the wire around a 30-gauge up to 3-5 coils. To increase the enzyme loading, a thread of cotton is preferably passed through the coil chamber. The resulting coil unit had an outer diameter of 0.7 mm and an inner diameter of 0.3 mm and a length of ca. 1 mm.

(2) Electrochemical Polymerization of PDD Film

The internal interference-eliminating layer, i.e. poly(ophenylenediamine) or poly(m-phenylenediamine) film was electropolymerized potentiostatically at the surface of the coil-type platinum-iridium wire at 0.7 V vs SCE for 5 min in a PBS solution containing 5 mmol/L o-phenylenediamine, 20 U/ml GOD, 1(1/ml 0.25% glutaraldehyde and 10 (l/ml of 1% GOD stabilization agent (poly-L-lysine hydrobromide). The resulting electrode was dried at 60° C. for one hour.

(3) Enzyme Immobilization

The cross-linking enzyme layer (GOx) was formed at the surface of the coil-type platinum-iridium wire or the PDD film by dip-coating the electrode in an enzyme solution containing 1.5 KU/ml GOD, 40 mg/ml bovine serum albumin and 0.6% glutaraldehyde. The resulting enzyme layer needs to dry at room temperature for a half hour before being imposed another coating.

(4) Coating of Nafion Interference-Eliminating Layer

A Nafion solution of lower aliphatic alcohols was in the original concentration as received, i.e. 5%. The Nafion layer was coated to the immobilized enzyme layer by dip-coating then annealed at 120° C. for 30 min as previously reported (Biosensors & Bioelectronics 13(2), 133-145 (1998)).

(5) Coating of Epoxy-Containing Polymer Membrane

The total concentration of epoxy-containing polymer solution (solvents: chloroform for PC; THF for PU and PVC) preferably was in the range of 1.4-2.0% (w/v), including all solvates, for example Brij 30 and plasticizers. The composition and ratios of every component were specified in individual cases. The epoxy-containing membrane can be dried at room temperature for 24 hours or at 120° C. for one hour. The thickness of the PDD film was self-limited by electropolymerization and was approximately 100 nm. The thickness of immobilized enzyme layer, Nafion layer and epoxy-enhanced polymer layer was roughly adjusted by dip-coating numbers. In the present examples, immobilized enzyme layer, Nafion layer and epoxy-enhanced polymer layer used 3-4, 1-2 and 2-3 times of dip-coatings, respectively.

(6) Assembly of Coil-Type Sensors

The two ends of the sensing element were sealed by electrically-insulating sealant and then combined with the coiled Ag/AgCl electrode coated with a thin layer polyurethane film containing 20% epoxy resin. Experimental methods Measurements were conducted in a 10 ml glass cell under room temperature at the (0.7V polarizing potential vs. Ag/AgCl or SCE. New sensors were conditioned for at least 2 days in a BPS or 5 mM glucose solution then continually polarized until the minimum background current is reached. Glucose biosensors for lifetime investigations were incubated in a 5 mmol/L glucose/PBS solution and sensitivities were intermittently measured. When not being specified, the response time is represented as the desired time reaching up to 95% of the maximum current when glucose concentration changes from 5 mM to 15 mM. Calibration plots were obtained by glucose step increment method, which various step concentrations were made by adding a proper volume of a 100 mM glucose/PBS solution. The chemical interference test was performed by determining the current signal variation causing by adding interferent solutions to the 5 mM glucose/PBS solution. The influences of biological matrix on the response behavior of the new sensing element were examined by observing the response sensitivity reduction and current signal stability in bovine sera.

Experimental Results (A) Influence of Polymer on Response Characteristics

Figure 2:
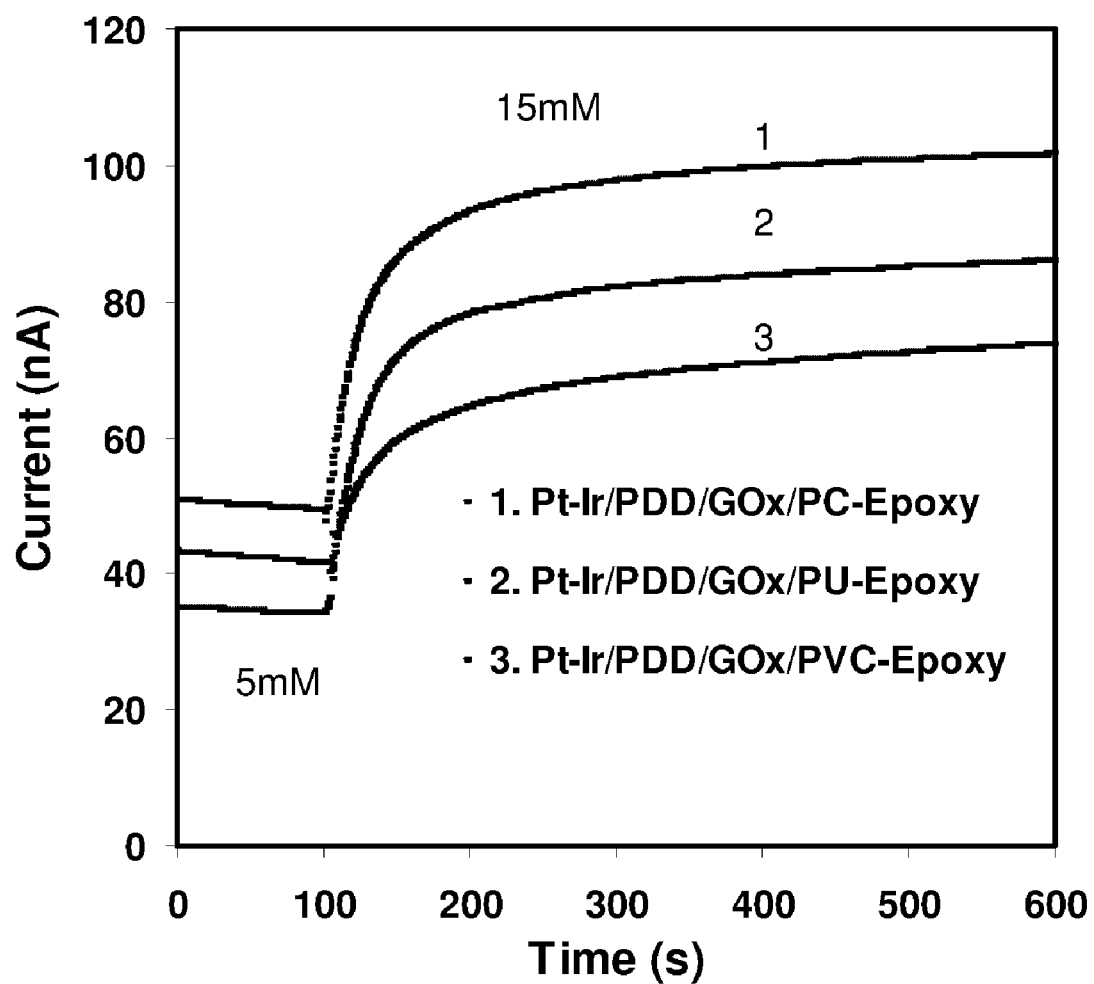
FIG. 2 is an illustration of the current response curves of various epoxy-based glucose sensors in accordance with the present invention. Epoxy-polymer composition: 38% Epoxy-56% Polymer6% Brij30; Glucose concentration of the measured solution was varied from 5 mM to 15 mM.

FIG. 2 shows the current increases of three sorts of PtIr/PDD/GOx/epoxy-Polymer glucose sensors when the glucose concentration of the measured solution rises up to 15 mM from 5 mM, where polymer included PC, PU and PVC. Comparatively, the PC-epoxy-based sensor shows a faster response as well as a higher response sensitivity, indicating the PC-epoxy membrane has good permeability. Unfortunately, the epoxy membrane based on the present polycarbonate is not strong enough and the lifetime of sensors is short.

(B) Response Behavior of Epoxy-PVC-Based Sensors

Figure 3:
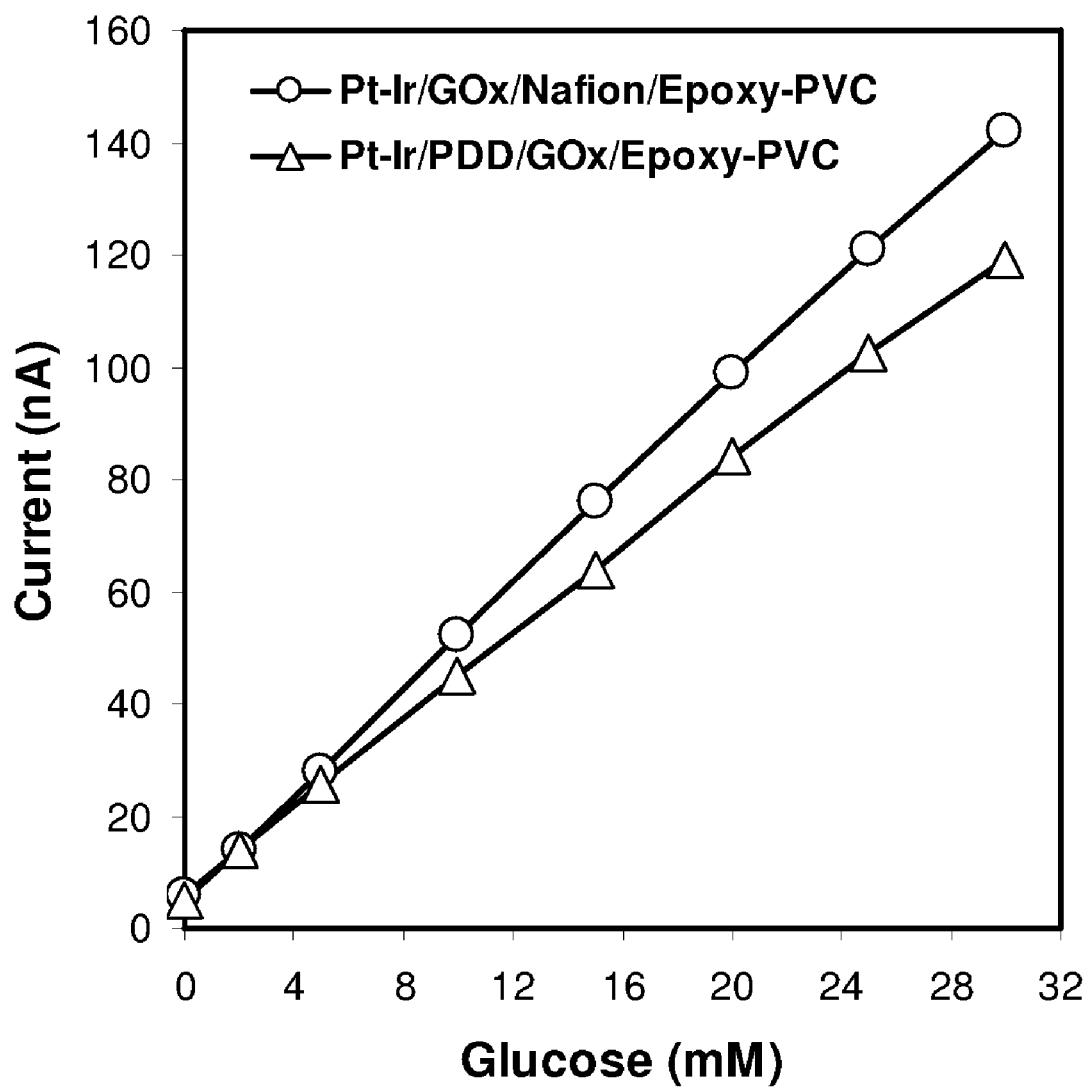
FIG. 3 is an illustration of the calibration plots of epoxy-PVC-based glucose sensors in accordance with the present invention. Epoxy-PVC composition: 31.6% PVC31.6% Epoxy 10.5% IMP21.0% AL5.3% Brij 30

FIG. 3 shows the relationship of response current and glucose concentration of two epoxy-PVC-based sensors. One has an internal PDD film while another has a Nafion middle layer. Whatever is used as the interference-eliminating layer, the sensors shows a wide response linearity range, at least 1-30 mM. The typical response time for such sensors is in the range of 100-300 seconds, depending upon the thickness of the sensing element. The average lifetime of the sensor is 4 months and can exceed 6 months when the epoxy-PVC membrane is formed in an excellent quality. It was found that the thicker epoxy-PVC membrane has a longer lifetime, implying the outer epoxy-PVC membrane plays a critical role in extending the lifetime of the sensor.

Under the electron microscope, the porosity of epoxy-Polymer membrane was observed. Meantime, minor defects can be found. Development of Defects may be the major cause that results in the function failure of some sensors. Minor defects can be readily formed at the uneven surface of a coil-type sensor. When a planar electrode surface is used, membrane quality can be further improved.

When epoxy-PVC sensors were continuously polarized in bovine serum, the response keeps decreasing until loss of response. This is attributed to the high hydrophobicity of PVC and can be improved by adding a PU layer to the epoxy-PU layer.

(C) Response Behavior of Epoxy-PU-Based Sensors

Figure 4:
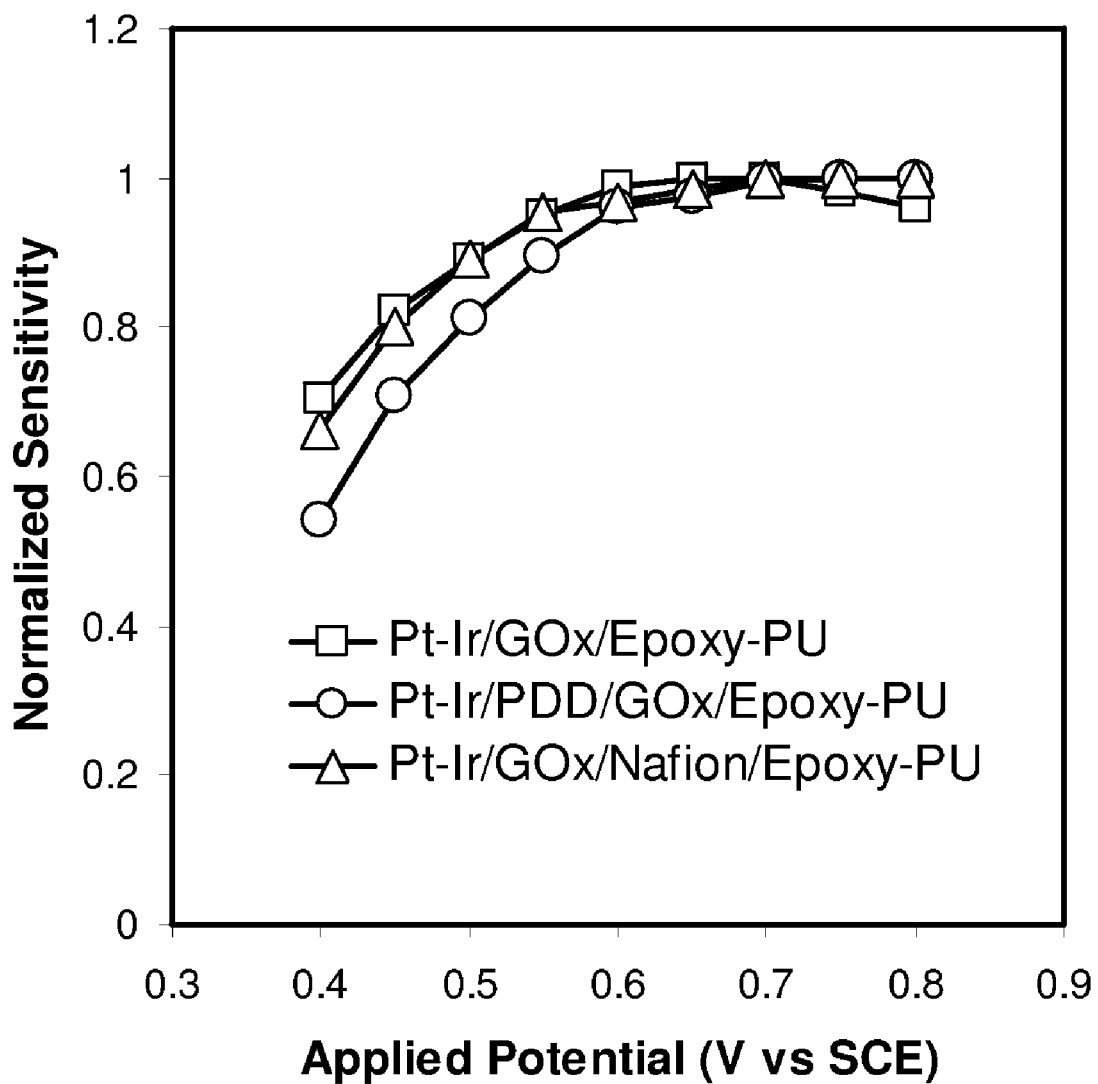
FIG. 4 is an illustration of the current-potential dependence of epoxy-PU-based glucose sensors in accordance with the present invention. Epoxy-PU composition: 44% Epoxy-44% PU12% Brij30

FIG. 4 shows the current-potential dependence of three sorts of epoxy-PU-based sensors. All these sensors can produce excellent responses in a wide potential range. Thus, a low polarization potential at which the oxidation of L-ascorbic acid and acetaminophen less occurs may be selected for these sensors, typically e.g. 0.5V. According to FIG. 4, it can be concluded that neither an internal PDD film nor a Nafion layer causes significant difference in the potential property of the sensors.

Figure 5:
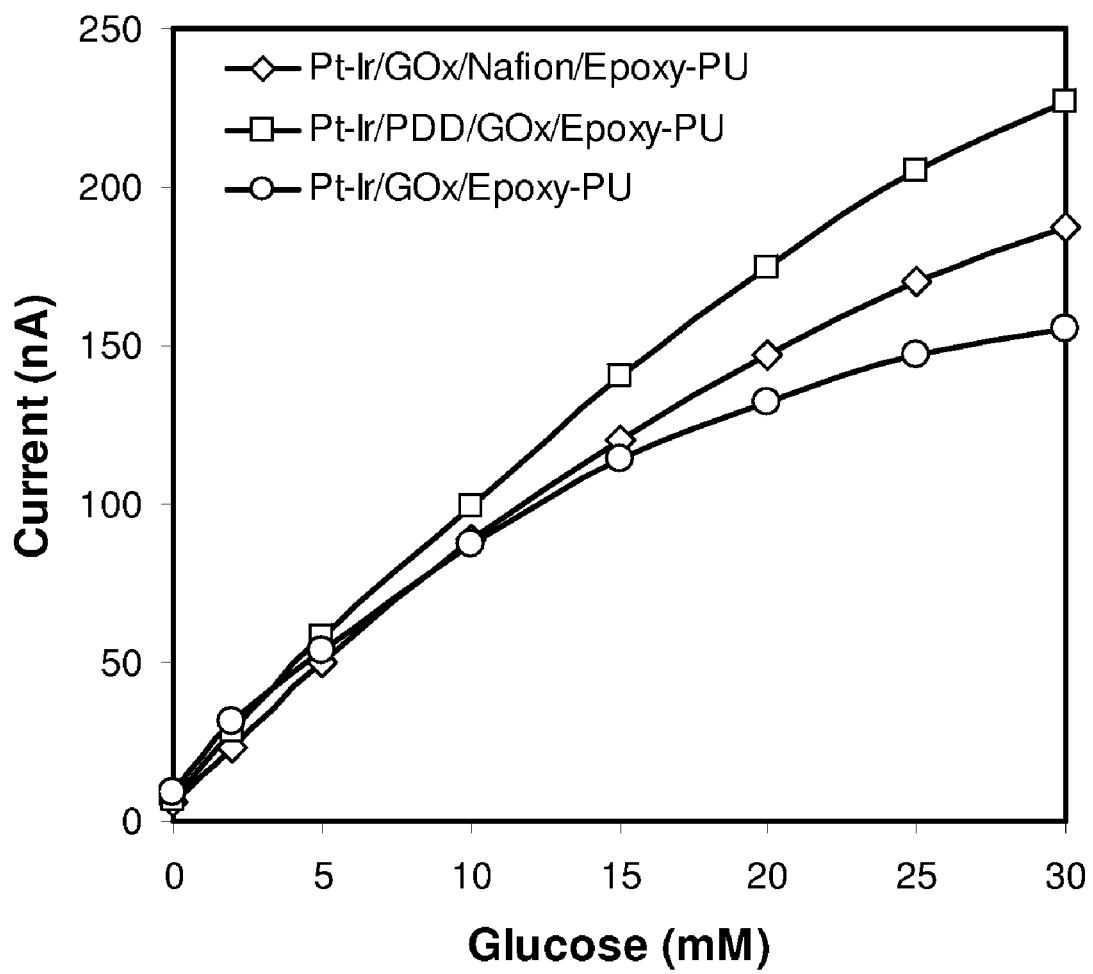
FIG. 5 is an illustration of the calibration plots of epoxy-based glucose sensors in accordance with the present invention. Epoxy-PU composition: 44% Epoxy-44% PU12% Brij30

FIG. 5 further shows the linearity of these sensors. Comparing with FIG. 3, apparently, the epoxy-PU based sensors have poorer linearity than the epoxy-PVC-based sensors. Involvement of PDD and Nafion films can extend the linearity at a certain extent, but not significantly. Nevertheless, a linearity of 1-20 mM can satisfy the measurement requirement of biological specimens.

Under the electron microscope, the epoxy-PU membrane was observed to be uniform and compact and the membrane quality was obviously better than the epoxy-PVC. The average lifetime of the sensor with an epoxy-PU outer membrane is approximately 5 months, extremely over 8 months.

(D) Discussion

Figure 7:
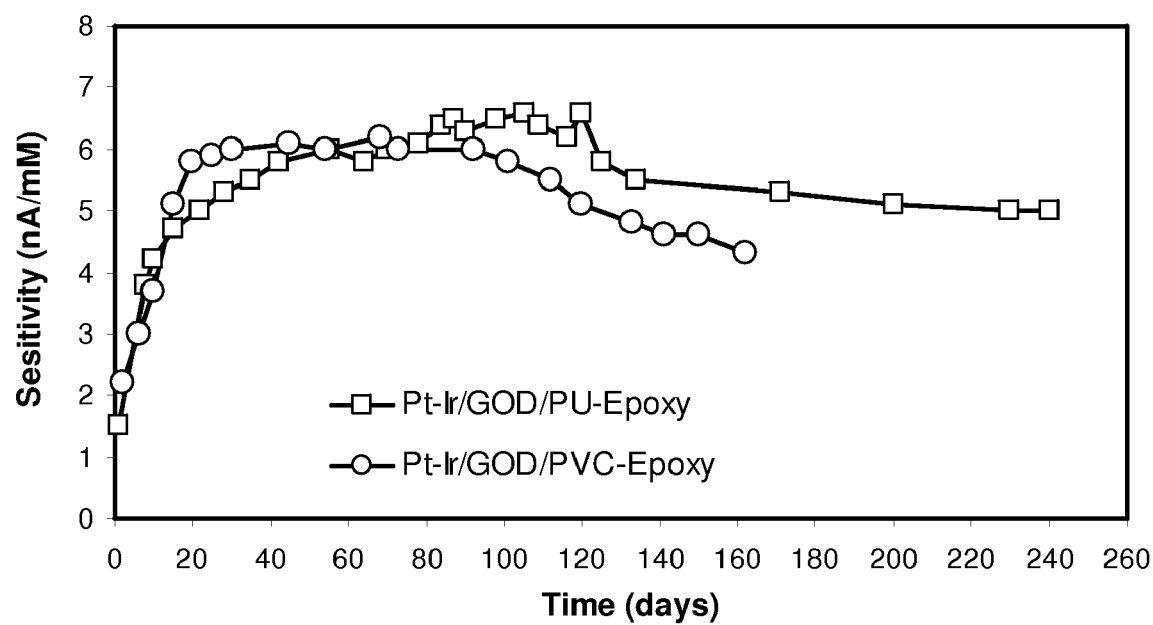
FIG. 7 is an illustration of the long-term records of sensitivity for two epoxy-based glucose sensors in accordance with the present invention.

FIG. 7 records the sensitivity values of an epoxy-PVC sensor and an epoxy-PU sensor in different days. To exclude the possible contribution of other polymer membranes in the lifetime, both two sensors do not include PDD and Nafion films. We also examined Nafion, PVC, PU and PC-based control sensors at the same experimental conditions and the results are listed in Table 1.

TABLE 1

| Sensor | | Linearity (mM) | Response time (Second) | Lifetime |
|---|---|---|---|---|
| Control 1 | Pt-Ir/GOx/Nafion | 1-25 | 30-100 | 2-3 months |
| Control 2 | Pt-Ir/GOx/PC | 0.5-15 | 10-80 | 2-3 weeks |
| Example 1 | Pt-Ir/GOx/Epoxy-PC | 1-20 | 40-130 | 1-2 months |
| Control 3 | Pt-Ir/GOx/PVC | 1-50 | 30-110 | 1-2 months |
| Example 2 | Pt-Ir/GOx/Epoxy-PVC | 1-30 | 100-300 | 3-6 months |
| Control 4 | Pt-Ir/GOx/PU | 1-25 | 20-100 | 1-2 months |

TABLE 1-continued

| Sensor | | Linearity (mM) | Response time (Second) | Lifetime |
|---|---|---|---|---|
| Example 3 | Pt-Ir/GOx/Epoxy-PU | 1-20 | 100-300 | 4-8 months |

Interference investigations were focused on L-ascorbic acid, uric acid and acetaminophen. In Table 1, epoxy-PVC membrane includes 31.6% PVC, 31.6% epoxy, 10.5% IMP, 21.0% AL, 5.3% Brij 30 and epoxy-PU membrane includes 44% PU, 44% epoxy, 12% Brij30. The listed data mean the increase of glucose concentration caused by 1 mM interferents. Unlike PVC, PU itself does not have interference eliminating ability and therefore specially needs an addition layer. The layer can be composed of either PDD or Nafion which are effective to block L-ascorbic, uric acid and most acetaminophen.

TABLE 2

| Sensor | L-Ascorbic | Acetaminophen | Uric Acid |
|---|---|---|---|
| Pt-Ir/GOx/Epoxy-PVC | +1.0 ± 0.4 | +11.2 ± 3.0 | +1.0 ± 0.4 |
| Pt-Ir/GOx/Epoxy-PU | +3.1 ± 0.4 | +9.0 ± 1.5 | +3.3 ± 0.5 |
| Pt-Ir/GOx/Nafion/Epoxy-PVC | +0.6 ± 0.1 | +2.0 ± 0.5 | +0.6 ± 0.3 |
| Pt-Ir/GOx/Nafion/Epoxy-PU | +1.6 ± 0.4 | +2.8 ± 1.2 | +3.4 ± 0.5 |
| Pt-Ir/PDD/GOx/Epoxy-PVC | +0.2 ± 0.1 | +2.5 ± 0.4 | +0.5 ± 0.2 |
| Pt-Ir/PDD/GOx/Epoxy-PU | +0.8 ± 0.3 | +2.2 ± 0.3 | +1.5 ± 0.4 |
| Pt-Ir/PDD/GOx/Nafion/Epoxy-PU | +0.6 ± 0.2 | +2.0 ± 0.2 | +0.5 ± 0.2 |

Figure 6:
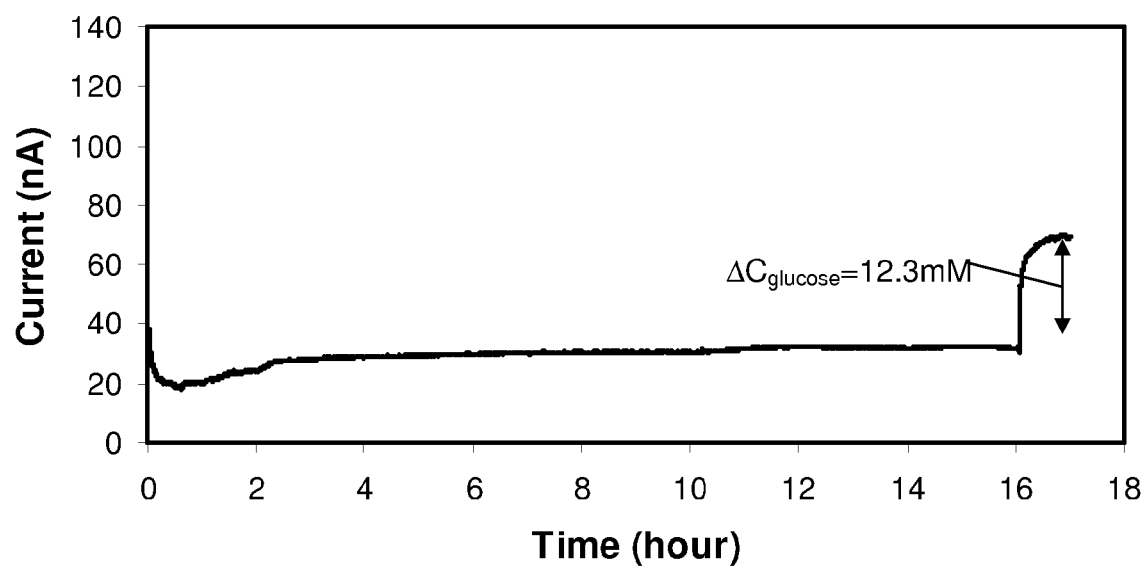
FIG. 6 is an illustration of the long-term response of a Pt—Ir/PDD/GOx/Epoxy-PU glucose sensor in bovine serum in accordance with the present invention. At the $16^{th}$ hour, a 100 mM glucose solution was added into the serum sample. Epoxy-PU composition: 44% Epoxy-44% PU 12% Brij 30

Since epoxy resins are also highly biocompatible, epoxy-PU is almost ideal to be used as the outmost layer of biosensors. The epoxy-PU membrane can effectively replace polyurethane coating in implantation applications but have less risk of peeling off in bodies due to the good adhesion of epoxy resins. FIG. 6 records the response stability of an epoxy-PU-based sensor in bovine serum as continually polarized at 0.7V vs Ag/AgCl. The instable varying of signals in the beginning 2 hours reflects the warm-up process of serum from 5° C. to 24° C. After 2 hours, the signal keeps in a stable level. At the 16th hour, a 100 mM glucose solution was added into serum and made a 12.3 mM increase of glucose concentration (measured by using FreeStyle strips). The signal increasing was observed despite the response is much slower than that in solutions ($T_{90}\%$=28 min for an increase of 10 mM glucose). The sensitivity in serum is about 40% of the sensitivity in solutions. The lower and slower response in biological matrix can be attributed to the deposition of protein at the membrane surface.

The epoxy sort and content in the polymer blend have profound influences on the properties of the resulting membrane, e.g. durability, flexibility and permeability. For the epoxy resin used in the present example, the membrane became fragile as its weight percentage in the blend exceeded 60%. Ideally, the range is within 20-40%. However, as different epoxy resins are used, this epoxy content can be changed. Meantime, the selection of polymer is also critical. Because of the limitation of time and experimental conditions, we are not able to try more epoxy resins and polymers. However, it should be understood that the materials used in the present experiments may be not the best options. Therefore, there is still a big space for improvement of membrane component and compositions. Even so, the lifetime of the epoxy-based sensors described in the present invention is much longer than those of the reported sensors. Basing on the invented epoxy-polymer, new substrate materials, e.g. titanium plating metal or alloy, which are excellently biocompatible, can be used to construct implantable biosensors. With the progress of the research, new applications may be discovered.

What is claimed is:

1. A permeable membrane for an implantable biosensor comprising a cured product of an epoxy resin enhanced polymer composition comprising:
   at least one epoxy resin adhesive comprising an epoxy resin and a curing agent for curing the epoxy resin,
   at least one polymer different from the epoxy resin adhesive, and
   at least one water-immiscible organic solvent;
   wherein the at least one epoxy resin adhesive accounts for about 10% to about 60% by weight of the permeable membrane; and
   wherein the at least one polymer different from the epoxy resin adhesive accounts for about 30% to about 80% by weight of the permeable membrane.

2. The permeable membrane of claim 1 wherein the epoxy resin enhanced polymer composition further comprises a polyethylene oxide-containing block copolymer wherein the polyethylene oxide-containing block copolymer accounts for about 5% to about 15% by weight of the permeable membrane.

3. The permeable membrane of claim 1 wherein the epoxy-resin enhanced polymer composition optionally comprises one or more plasticizers wherein the one or more plasticizers accounts for up to about 30% by weight of the permeable membrane.

4. The permeable membrane coating of claim 3 wherein the one or more plasticizers is selected from the group consisting of dibutyl phthalate, butyl sebacate and triphenyl phosphate.

5. The permeable membrane of claim 1 wherein the epoxy resin enhanced polymer composition further comprises a polyethylene oxide-containing block copolymer and optionally comprises one or more plasticizers;
   wherein the at least one epoxy resin adhesive accounts for about 30% to about 50% by weight of the permeable membrane;
   wherein the at least one polymer different from said epoxy resin adhesive accounts for about 40% to about 70% by weight of the permeable membrane;
   wherein the polyethylene oxide-containing block copolymer accounts for about 5% to about 10% by weight of the permeable membrane; and
   wherein the one or more plasticizers accounts for up to about 30% by weight of the permeable membrane.

6. The permeable membrane of claim 1 wherein the epoxy resin adhesive is selected from the group consisting of heat-curable epoxy resin adhesives, light-curable epoxy resin adhesives and radiation-curable epoxy resin adhesives.

7. The permeable membrane of claim 1 wherein the epoxy resin adhesive is a heat-curable epoxy resin adhesive which can be cured at a temperature less than 120° C.

8. The permeable membrane of claim 1 wherein the epoxy resin adhesive is selected from the group consisting single component epoxy resin adhesives, two component epoxy resin adhesives and multiple component epoxy resin adhesives.

9. The permeable membrane of claim 1 wherein the polymer is selected from the group consisting of polyurethane, polyester, phosphorylcholine-containing copolymer, polydimethylsiloxane, polycarbonate, poly(vinyl chloride), cellulose acetate, polyallylamine-polyaziridine, polyvinylidene chlorides, polyvinylidene-acrylonitrile copolymer, polyacrylate, polymethylacrylate and polystyrene.

10. A multilayered sensing element for implantable long term biosensors comprising:
    an immobilized enzyme layer formed on an electrode surface; and
    a permeable membrane comprised of a cured product of an epoxy resin enhanced polymer composition whereby the permeable membrane is external to and surrounding the immobilized enzyme layer;
    the epoxy resin enhanced polymer composition comprising:
    at least one epoxy resin adhesive comprising an epoxy resin and a curing agent for curing the epoxy resin,
    at least one polymer different from the epoxy resin adhesive, and
    at least one organic solvent;
    wherein the at least one epoxy resin adhesive accounts for about 10% to about 60% by weight of the permeable membrane; and
    wherein the at least one a polymer different from the epoxy resin adhesive accounts for about 30% to about 80% by weight of the permeable membrane.

11. The multilayered sensing element of claim 10 wherein the epoxy resin enhanced composition further comprises a polyethylene oxide-containing block copolymer wherein the polyethylene oxide-containing block copolymer accounts for about 5% to about 15% by weight of the permeable membrane.

12. The multilayered sensing element of claim 10 wherein the epoxy resin enhanced composition optionally comprises one or more plasticizers wherein the one or more plasticizers accounts for up to about 30% by weight of the permeable membrane.

13. The multilayered sensing element of claim 10 further comprising an interference-eliminating layer spaced between the immobilized enzyme layer and the epoxy resin composition.

14. The multilayered sensing element of claim 13 wherein the interference-eliminating layer is a persulfonate ionomer.

15. The multilayered sensing element of claim 10 wherein the enzyme of the immobilized enzyme layer is selected from the group consisting of glucose oxidase and lactate oxidase.

* * * * *

UNITED STATES PATENT AND TRADEMARK OFFICE
CERTIFICATE OF CORRECTION

PATENT NO. : 7,799,191 B2  
APPLICATION NO. : 12/015614  
DATED : September 21, 2010  
INVENTOR(S) : Bazhang Yu and Francis Moussy It is certified that error appears in the above-identified patent and that said Letters Patent is hereby corrected as shown below:

In the Specifications:

Column 1, Line 17, delete lines 17-18 and replace with
--This invention was made with government support under grant number EB001640 awarded by the National Institutes of Health. The government has certain rights in the invention.--.

Signed and Sealed this
Thirtieth Day of April, 2013

Teresa Stanek Rea
*Acting Director of the United States Patent and Trademark Office*